US008039258B2

(12) United States Patent
Harris et al.

(10) Patent No.: US 8,039,258 B2
(45) Date of Patent: Oct. 18, 2011

(54) TISSUE-ENGINEERING SCAFFOLDS CONTAINING SELF-ASSEMBLED-PEPTIDE HYDROGELS

(75) Inventors: Ian Ross Harris, Belle Mead, NJ (US); Alexander M. Harmon, Clinton, NJ (US); Laura J. Brown, Hamilton Square, NJ (US); Anna Gosiewska, Skillman, NJ (US)

(73) Assignee: Ethicon, Inc., Somerville, NJ (US)

( * ) Notice: Subject to any disclaimer, the term of this patent is extended or adjusted under 35 U.S.C. 154(b) by 991 days.

(21) Appl. No.: 10/951,357

(22) Filed: Sep. 28, 2004

(65) Prior Publication Data
US 2008/0145934 A1 Jun. 19, 2008

(51) Int. Cl.
C12N 5/06 (2006.01)
(52) U.S. Cl. ...................................... 435/404
(58) Field of Classification Search .................. None
See application file for complete search history.

(56) References Cited

U.S. PATENT DOCUMENTS

| | | | |
|---|---|---|---|
| 5,284,766 A | 2/1994 | Okano et al. | |
| 5,670,483 A | 9/1997 | Zhang et al. | 514/14 |
| 5,955,343 A | 9/1999 | Holmes et al. | 435/240.1 |
| 6,171,610 B1 | 1/2001 | Vacanti et al. | |
| 6,179,872 B1 | 1/2001 | Bell et al. | |
| 6,333,029 B1 | 12/2001 | Vyakarnam et al. | 424/93.1 |
| 6,355,699 B1 | 3/2002 | Vyakarnam et al. | |
| 6,366,149 B1 | 4/2002 | Lee et al. | 327/276 |
| 6,495,645 B1 | 12/2002 | Okano et al. | |
| 6,511,511 B1 | 1/2003 | Slivka et al. | |
| 6,534,084 B1 | 3/2003 | Vyakarnam et al. | 424/443 |
| 6,599,323 B2 | 7/2003 | Melican et al. | 623/23.72 |
| 2002/0022676 A1 | 2/2002 | He et al. | |
| 2002/0151050 A1 | 10/2002 | Vacanti et al. | |
| 2002/0160471 A1 | 10/2002 | Kisiday et al. | 435/177 |
| 2002/0182241 A1 | 12/2002 | Borenstein et al. | |
| 2003/0138950 A1 | 7/2003 | McAlister et al. | |
| 2003/0228693 A1 | 12/2003 | Tsuzuki et al. | |
| 2004/0137619 A1 | 7/2004 | Tsuzuki et al. | |
| 2005/0010940 A1 | 1/2005 | Guo | 720/659 |
| 2005/0054098 A1 | 3/2005 | Mistry et al. | |
| 2005/0058631 A1 | 3/2005 | Kihm et al. | |
| 2005/0181973 A1* | 8/2005 | Genove et al. | 514/2 |
| 2006/0005473 A1 | 1/2006 | Friedman | 52/640 |
| 2006/0153815 A1 | 7/2006 | Seyda et al. | |
| 2006/0166361 A1 | 7/2006 | Seyda et al. | |
| 2006/0171930 A1 | 8/2006 | Seyda et al. | |

FOREIGN PATENT DOCUMENTS

| | | |
|---|---|---|
| EP | 1 316 322 A1 | 6/2003 |
| WO | WO 00/43355 | 7/2000 |
| WO | 02/062969 A2 | 8/2002 |
| WO | 03/054146 A2 | 7/2003 |
| WO | 03/070749 A2 | 8/2003 |
| WO | 2004/003561 A1 | 1/2004 |
| WO | 2004/007532 A2 | 1/2004 |
| WO | 2004/072104 A2 | 8/2004 |
| WO | WO-2005/014615 A2 | 2/2005 |
| WO | 2005/034624 A2 | 4/2005 |

OTHER PUBLICATIONS

Kisiday et al (PNAS. Jul. 23, 2002; 99(15):9996-10001).*
Ratner et al. (Annu. Rev. Biomed. Eng. 2004; 6:41-75).*
Kopeček (European Journal of Pharmaceutical Sciences. 2003; 20: 1-16).*
Saatchi—MIT Thesis (M.S.) 2004—A novel osteochondral composite consisting of a self-assembling peptide hydrogel and 3D printed polycaprolactone scaffold : potential for articular cartilage repair.*
Yoshida et al. (Cell Adhesion & Migration. Apr./May/Jun. 2007; 1(2): 92-98).*
Fields, G. B., "Induction of Protein-like Molecular Architecture by Self-assembly Processes," *Bioorganic & Medicinal Chemistry*, 1999, 7 (1), 75-81.
Gosiewska, A. et al., "Development of a three-dimensional transmigration assay for testing cell-polymer interactions for tissue engineering applications," *Tissue Engineering*, Jun. 2001, 7(3), 267-277.
Hartgerink, J. D. et al., "Peptide-amphiphile nanofibers: a versatile scaffold for the preparation of self-assembling materials," *PNAS*, Apr. 16, 2002, 99(8), 5133-5138.
Kisiday, J. et al., "Self-assembling peptide hydrogel fosters chondrocyte extracellular matrix production and cell division: Implications for cartilage tissue repair," *PNAS*, Jul. 23, 2002, 99(15), 9996-10001.
Nowak, A. P. et al., "Rapidly recovering hydrogel scaffolds from self-assembling diblock copolypeptide amphiphiles," *Nature*, May 23, 2002, 417(6887), 424-428.
Ryadnov, M. G. et al., "Engineering the morphology of a self-assembling protein fibre," *Nat. Mater.*, 2003, 2(5), 329-332.
Allcock, H.R. et al., "Synthesis of Poly[(Amino Acid Alkyl Ester)Phosphazenes]1-3," *Macromolecules*, 1977; 10(4):824-830.
Anseth, K.S. et al., "In Situ Forming Degradable Networks and Their Application in Tissue Engineering and Drug Delivery," *J. of Controlled Release*, 2002; 78:199-209.
Domb, A. et al., "Degradable Polymers for Site-Specific Drug Delivery," *Polymers for Advanced Technologies*, 1992; 3:279-92.
Friedman, J.A. et al., "Biodegradable Polymer Grafts for Surgical Repair of the Injured Spinal Cord," *Neurosurgery*, 2002; 51(3):742-52.
Hutmacher, D.W., "Scaffold Design and Fabrication Technologies for Engineering Tissues—State of the Art and Future Perspectives," *J. Biomater. Sci. Polymer Edn.*, 2001;12(1):107-24.

(Continued)

*Primary Examiner* — Scott Long
(74) *Attorney, Agent, or Firm* — Patton Boggs LLP

(57) ABSTRACT

The present invention is directed to tissue-engineering scaffolds containing both a microporous scaffold made from a biocompatible material suitable for use in tissue-engineering scaffolds and a nanofiberous, nanoporous hydrogel formed from a self-assembling peptide, where at least a portion of the hydrogel is disposed within the pores of the microporous scaffold, thus providing tissue-engineering scaffolds having average pore diameters in the nanometer range and that provide both mechanical properties suitable for implantation into a body of a mammal and excellent tissue response once implanted in the body.

14 Claims, No Drawings

OTHER PUBLICATIONS

Ito, Y. et al., "A Quantitative Assay Using Basement Membrane Extracts to Study Tumor Angiogenesis in Vivo," *Int. J. Cancer*, 1996; 67:148-152.

Kokufuta, E. et al., "Effects of Surfactants on the Phase Transition of Poly(N-isopropylacrylamide) Gel," *Macromolecules*, 1993; 26:1053-59.

Ma, P.X. et al., "Synthetic Nano-Scale Fibrous Extracellular Matrix," *J. Biomed Mater Res.*, 1999; 46(1):60-72.

Newman, K.D. et al., "Poly(D,L lactic-co-glycolic acid) Microspheres as Biodegradable Microcarriers for Pluripotent Stem Cells," *Biomaterials*, 2004; 25:5763-5771.

Nicosia, R.F. et al., "Modulation of Microvascular Growth and Morphogenesis by Reconstituted Basement Membrane Gel in Three-Dimensional Cultures of Rat Aorta: A Comparative Study of Angiogenesis in Matrigal, Collagen, Fibrin, and Plasma Clot," *In Vitro Cell Dev. Biol.*, 1990; 26(2):119-128.

Wang, D. et al., "Synthesis and Characterization of a Novel Degradable Phosphate-Containing Hydrogel," *Biomaterials*, 2003; 24:3969-3980.

Xu, A. et al.,"Soft, Porous Poly(D,L lactide-co-glycotide) Microcarriers Designed for Ex Vivo Studies and for Transplantation of Adherent Cell Types including Progenitors," Annals of the New York Academy of Sciences, 2001, vol. 944: 144-159.

Apr. 11, 2008 Office Action issued by the European Patent Office for EP Application No. 05 798 654.9.

International Search Report for PCT/US2005/034252.

Holmes, et al., Extensive Neurite Outgrowth and Active Synapse Formation on Self-Assembling Peptide Scaffolds, *PNAS*, 97(12):6728-6733, 2000.

Niederauer, et al., Evaluation of Multiphase Implants for Repair for Focal Osteochondral Defects in Goats, *Biomaterials*, 21:2561-2574, 2000.

\* cited by examiner

SEQUENCE LISTING

```
<160> NUMBER OF SEQ ID NOS: 4

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct

<400> SEQUENCE: 1

Arg Ala Asp Ala Arg Ala Asp Ala Arg Ala Asp Ala Arg Ala Asp Ala
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct
```

```
-continued

<400> SEQUENCE: 2

Lys Leu Asp Leu Lys Leu Asp Leu Lys Leu Asp Leu
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetic Construct

<400> SEQUENCE: 3

Ala Ala Ala Ala Gly Gly Gly Ser
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic Construct

<400> SEQUENCE: 4

Cys Cys Cys Cys Gly Gly Gly Ser
1               5
```

TISSUE-ENGINEERING SCAFFOLDS CONTAINING SELF-ASSEMBLED-PEPTIDE HYDROGELS

FIELD OF THE INVENTION

The present invention relates to tissue engineering scaffolds made of microporous scaffolds containing nanofibrous, nanoporous hydrogels formed from self-assembling peptides.

BACKGROUND OF THE INVENTION

Numerous scaffolds have been developed for tissue engineering applications. These scaffolds provide a template on which cells can migrate, divide, secrete new matrix and differentiate. Typical tissue engineering scaffolds are porous and can be categorized as having pores on either a micrometer scale, i.e. microporous, or a nanometer scale, i.e. nanoporous. Scaffolds having pores on a micrometer scale, or having average pore diameter of about 10 to 1000 microns, are composed of a variety of biocompatible materials including metals, ceramics and polymers. Such scaffolds include solid-cast structures, open-pore foams, felts, meshes, nonwovens, woven and knitted constructs. The mechanical and conformational properties can be chosen by composition of the material and the design of the scaffold. Desirable mechanical properties include the ability to be sutured in place and good handling strength.

Composition, design and construction of the scaffold are also important to how tissue responds to the scaffold. The scaffold can be shaped to maximize surface area, to allow adequate diffusion of nutrients and growth factors to cells present in or growing into it. For example, the maximum distance over which adequate diffusion through densely packed cells can occur is in the range of about 100 to 300 microns, under conditions similar to those that occur in the body, wherein nutrients and oxygen diffuse from blood vessels moving into the surrounding tissue. Taking these parameters into consideration, one of skill in the art would configure a scaffold having pores on a micrometer scale as having sufficient surface area for the cells to be nourished by diffusion until new blood vessels interdigitate the implanted scaffold.

Scaffolds having pores on a nanometer scale, e.g. having average pore diameter of about 10 nanometers to 1 micron, are often composed of hydrogels. A hydrogel is a substance formed when a natural or synthetic organic polymer is cross-linked via covalent, ionic or hydrogen bonds to create a three-dimensional open-lattice structure, which entraps water molecules and forms a gel. Examples of materials that can be used to form a hydrogel include polyamides, methylcellulose, collagen, extracellular matrix (ECM), polysaccharides such as alginate, polyphosphazines, polyacrylates which are crosslinked tonically, high molecular weight poly(oxyalkylene ether) block copolymers such as those sold under the tradename PLURONCIS (BASF Corp., Mount Olive, N.J.), nonionic polymerized alkylene oxide compounds such as those sold under the tradename TETRONCIS (BASF Corp., Mount Olive, N.J.), or polyethylene oxide-polypropylene glycol block copolymers which are crosslinked by temperature or pH, respectively.

Hydrogels provide conformable, malleable, or injectable materials for administering cells into a tissue. They do not, however, have mechanical integrity. Synthetic hydrogels can be sterilized and do not have the risk of associated infectious agents. However, most synthetic hydrogels do not mimic the extracellular matrix and therefore do not direct cellular ingrowth or function. Hydrogels of natural extracellular matrix are biocompatible and can mimic the native cellular environment. However, natural hydrogels, unless made from autologous material, may elicit an immune response and may have associated infectious agents. Natural hydrogels, such as EHS mouse sarcoma basement membrane, or fibrin, have a fiber diameter of about 5 to about 10 nanometers, water content of about 80 to about 97 weight percent and average pore diameter of about 50 to about 400 nanometers.

It would be advantageous to provide a tissue engineering scaffold that provides benefits of both microporous and nanoporous scaffolds while avoiding problems associated with certain hydrogel scaffolds as noted above. The present invention provides such an advantage by selectively combining a microporous scaffold and a nanoporous scaffold, resulting in a tissue engineering scaffold possessing mechanical properties necessary for use and unexpected enhanced tissue ingrowth and vascularization.

SUMMARY OF THE INVENTION

The present invention comprises a tissue-engineering scaffold comprising a microporous scaffold comprising a biocompatible material suitable for use in tissue-engineering scaffolds and a nanofibrous, nanoporous hydrogel formed from a self-assembling peptide. At least a portion of the hydrogel is disposed within the pores of the microporous scaffold, thus providing tissue-engineering scaffolds having average pore diameters in the nanometer range and that provide both mechanical properties suitable for implantation into a body of a mammal and excellent tissue response once implanted in the body. The materials used to form the microporous scaffold and the nanofibrous, nanoporous hydrogel may have similar or different degradation times and may be seeded with cells or contain bioactive compounds.

DETAILED DESCRIPTION OF THE INVENTION

Tissue engineering often uses porous scaffolds to act as a template for cells to grow and produce new tissue. The present invention provides a novel scaffold that can be provided in a desired size and shape dependant on the contemplated use, has structural integrity such that it can be implanted and secured in the body of a mammal, and possesses excellent tissue ingrowth and vascularization properties. Tissue-engineering scaffolds of the present invention comprise a microporous scaffold, as described further herein, wherein at least a portion of the pores of the microporous scaffolds comprise a nanofibrous, nanoporous hydrogel formed from self-assembling peptides, hereinafter referred to as "self-assembled-peptide hydrogel" and as further described herein, disposed therein. Such scaffolds provide increased tissue ingrowth and vascularization, as compared to a microporous scaffold alone, or a microporous scaffold in combination with hydrogels not formed from self-assembled peptides, such as basement membrane extract.

Both the microporous scaffold and the nanoporous self-assembled-peptide hydrogel may be vehicles for slow-diffusion drug delivery, as separation matrices, for supporting in vitro cell attachment and growth, for supporting artificial tissue, e.g., for in vivo use, and for other uses requiring permeable and water-insoluble material. The tissue-engineering scaffolds of the present invention may be applied to an open wound or surgically implanted.

The microporous scaffolds used in the present invention comprise pores having an average diameter of 1 to about 2,000 microns, or about 10 to about 1,000 microns, or about 10 to about 500 microns. The microporous scaffold may be in the form of solid-cast structures, open-pore foams, woven, nonwoven and knitted constructs. They can be prepared by methods including, without limitation, casting, lyophilization, spraying or machining, weaving, braiding, or knitting. The microporous scaffold typically has a thickness in the range of about 300 microns to about 3,000 microns, or in the range of about 500 microns to about 2,000 microns. The microporous scaffolds are made from biocompatible materials, such as polymers described herein below.

The microporous scaffolds may be made from a biodegradable polymer. As used herein, "biodegradable" refers to materials that degrade or break down upon interaction with a physiological environment into components that can be metabolized or excreted by the body over a period of time ranging from minutes to years, preferably less than one year. As used in reference to polymers, the term "degrade" refers to cleavage of the polymer chain, typically via hydrolysis or enzymatic cleavage, such that the molecular weight stays approximately constant at the oligomer level and particles of polymer remain following degradation. Although the polymers may be biodegradable, the scaffolds made from such polymers must maintain the structural integrity for a time required for their intended use.

The nanofibrous, nanoporous self-assembled-peptide hydrogels used in the present invention are macroscopic, or visible to the naked eye, and are formed from self-assembling peptides. The term peptide, as used herein, includes polypeptides and oligopeptides. The peptides can be chemically synthesized or they can be purified from natural and recombinant sources. Both homogeneous and heterogeneous mixtures of peptides characterized by the above-mentioned properties can form stable hydrogels. Peptides that are self-complementary and self-compatible can form hydrogels in a homogeneous mixture. Heterogeneous peptides, including those that cannot form hydrogels in homogeneous solutions, which are complementary and/or structurally compatible with each other can also self-assemble into macroscopic hydrogels.

Self-assembling peptides used in the present invention are distinct from other materials that form hydrogels. The art is replete with descriptions of self-assembling peptides and therefore the term itself is known to those skilled in the art involving such peptides. See, for example, Fields; *Induction of Protein-like Molecular Architecture by Self-assembly Processes*, Bioorganic & Medicinal Chemistry 7 (1999) 75-81, and as further described herein. A lipophilic moiety may be attached onto an $N^{th}$ amino group of a peptide chain, resulting in an amphiphilic peptide that has alternating repeating units of positively-charged moieties and negatively charged moieties. These peptides contain 50 percent charged residues and are characterized by their periodic repeats of alternating ionic hydrophilic and hydrophobic amino acids. The interaction between the distinct polar and non-polar surfaces facilitates self-assembly of the material into a nanofibrous hydrogel scaffold that can coat surfaces or encapsulate cells.

Self-assembling peptides combine the advantages of synthetic and natural hydrogels. Self-assembling peptides are synthetic and can be sterilized, do not have associated infectious agents and are non-immunogenic. Self-assembling peptides are biodegradable and mimic natural extracellular matrix (ECM) and therefore can interact with cells to influence cell morphology, gene expression, proliferation and cell migration. Self-assembling peptides used in the present invention typically have a fiber diameter of about 5 to about 10 nanometers. The self-assembled-peptide hydrogels have a water content of from about 98 to about 99.9 percent and comprise pores having an average pore diameter of about 10 to 1,000 nanometers, or an average pore diameter of about 50 to about 400 nanometers. Self-assembling peptides can be synthesized in large quantities using a process that produces high purity material with no risk of infectious agents that can be used in medical therapy.

Biocompatible materials that are suitable for use in the manufacture of microporous scaffolds used in the present invention include biodegradable and nonbiodegradable materials. Suitable nonbiodegradable materials include biocompatible metals such as stainless steel, cobalt chrome, titanium and titanium alloys, and bioinert ceramics, such as alumina, zirconia, and calcium sulfate.

Nonbiodegradable polymers that are suitable for use in the manufacture of microporous scaffolds used in the present invention include, without limitation, homopolymers and copolymers selected from aliphatic polyesters, polyacrylates, polymethacrylate, acyl-substituted cellulose acetates, non-biodegradable polyurethanes, polystyrenes, polyvinyl chloride, polyvinyl flouride, polyvinyl imidazole, chlorosulphonated polyolifins, polyethylene oxide, polyvinyl alcohol, polytetrafluoroethylene, nylon, silicon, and shape-memory materials such as poly(styrene-block-butadiene).

Biodegradable materials include ceramics, such as demineralized bone, calcium phosphates (hydroxyapatite, tricalcium phosphate), bioglass, and calcium carbonate, and polymers. Biodegradable polymers that are suitable for use in the manufacture of microporous scaffolds used in the present invention include, without limitation, homopolymers and copolymers selected from poly(lactic acid) (PLA), poly(L-lactic acid) (PLLA), poly(D-lactic acid) (PDLA), poly(glycolide), poly(glycolic acid) (PGA), polycaprolactone, poly(epsilon-caprolactone) (PCL), poly(lactide-co-glycolide) copolymer (PLA/PGA), poly(epsilon-caprolactone-co-glycolide) copolymer (PCL/PGA), poly(epsilon-caprolactone-co-L-lactide) copolymer (PCL/PLLA), polydioxanone (PDO), polygluconate, poly(lactic acid-co-ethylene oxide) copolymer, modified cellulose, collagen, polyhydroxybutyrate, poly(hydroxpriopionic acid), polyphosphoester, poly(alpha-hydroxy acid), polycarbonates, polyamides, polyanhydrides, polyamino acids, polyorthoesters and biodegradable polyurethanes.

Where tissue-engineering scaffolds of the present invention are biodegradable, the rate of biodegradability of the scaffold in the body environment is important. While the desired rate of biodegradability may be achieved by the use of biodegradable homopolymers or copolymers, the desired rate of biodegradability as would be determined by the absorption time under in vivo conditions can also be achieved by combining two different copolymers. For example, a copolymer of 35:65 epsilon-caprolactone and glycolide, a relatively fast biodegrading polymer, may be blended with 40:60 epsilon-caprolactone and L-lactide copolymer, a relatively slow biodegrading polymer, to form a microporous scaffold component having a pre-determined rate of biodegradability. Depending upon the processing technique used, the two constituents can be either randomly inter-connected, bi-continuous phases, or the constituents could have a gradient-like architecture in the form of a laminate-type composite with a well integrated interface between the two constituent layers. Accordingly, the composition and microstructure of these scaffolds can be optimized to regenerate or repair the desired anatomical features of the tissue that is being engineered.

In one embodiment as noted above, polymer blends may be used to form structures which transition from one composition to another composition in a gradient-like architecture. One of ordinary skill in the art will appreciate that polymer blends may be used for gradient effects such as different absorption profiles, stress response profiles, and different degrees of elasticity. See U.S. Pat. Nos. 6,333,029, 6366,149, and 6,534,084.

More than one microporous scaffold material can also be combined. For example, foam microporous scaffolds can be reinforced by a mesh or nonwoven felt to provide better mechanical properties and suture retention. Such scaffolds are described in U.S. Pat. No. 6,599,323, issued Jul. 23, 2003, the content of which is hereby incorporated in its entirety.

In one embodiment, biodegradable microporous scaffolds are made of synthetic, highly porous, biodegradable, non-woven sheets prepared from fibers comprising a polylactide-co-glycolide (PLA/PGA) copolymer with a lactide to glycolide ratio of 10:90 (10:90 PLA/PGA). Exemplary fibers are used in the manufacture of VICRYL® sutures, available from Ethicon, Inc., Somerville, N.J. Such nonwoven scaffolds typically have a porosity of from about 85 to about 99 percent, or about 90 to about 98 percent The nanofibrous, self-assembling peptides used in preparing self-assembled-peptide hydrogels utilized in the present invention have an average diameter of about 5 to about 50 nanometers. In certain embodiments the fiber diameter may be from about 5 to about 10 nanometers, or even about 5 to about 7 nanometers.

Self-assembling peptides useful in the present invention may include, for example, those discussed in U.S. Pat. Nos. 5,670,483 and 5,955,343; U.S. Patent Application No. 2002/0160471; PCT Application No. WO02/062969; Kisiday et al. Proc Natl Acad Sci U S A. (2002) 99; 9996-10001; Ryadnov M G, Woolfson D N Nat Mater. (2003) 2:329-32; Nowak A P et al. Nature. (2002) 417:424-8; Hartgerink J D et al. Proc Natl Acad Sci USA. 2002 99:5133-8; PCT Application Nos. WO03/054146, WO03/070749, WO04/003561, WO04/072104; and Fields, as noted herein above. The peptides have alternating hydrophobic and hydrophilic amino acids, comprise more than 8 amino acids, and may comprise at least 16 amino acids, and are complementary and structurally compatible with the microporous scaffold. Self-assembling peptides typically will not have more than about 30 to 50 amino acids.

The self-assembling peptides used for forming hydrogels used in the present invention include $NH_2$-RADARADARA-DARADA-COOH (SEQ ID NO:1), also know as RAD16, sold under the tradename PURAMATRIX (3-DMatrix, Inc., Cambridge, Mass.), and $NH_2$-KLDLKLDLKLDL-COOH (SEQ ID NO:2), also know as KLD, sold under the tradename PURAMATRIXCST (3-DMatrix, Inc., Cambridge, Mass.). The amino acid sequence of RAD16 is Arg-Ala-Asp-Ala-Arg-Ala-Asp-Ala-Arg-Ala-Asp-Ala-Arg-Ala-Asp-Ala (SEQ ID NO:1), while the amino acid sequence of KLD is Glu-Lys-Asp-Lys-Glu-Lys-Asp-Lys-Glu-Lys-Asp-Lys (SEQ ID NO:2).

Other self-assembling peptides which may be used to used form hydrogels in the present invention include peptide-amphiphile nanofibers comprising peptide fragments AAAAGGGS (SEQ ID NO:3) or CCCCGGGS (SEQ ID NO:4) disclosed in Hartgerink J D et al. Proc Natl Acad Sci USA. 2002 99:5133-8; PCT Application Nos. WO03/054146, WO03/070749, WO04/003561, WO04/072104. The amino acid sequence of AAAAGGGS is Ala-Ala-Ala-Ala-Gly-Gly-Gly-Ser (SEQ ID NO:3), while the amino acid sequence of CCCCGGGS is Csy-Csy-Csy-Csy-Gly-Gly-Gly-Ser (SEQ ID NO:4).

These nanofibrous, self-assembling peptides are synthesized in relatively short oligopeptide fragments that self-assemble into nanofibers on a scale similar to the in vivo extracellular matrix (ECM). A RAD16 fragment is about 5 nanometers in length. The self-assembly of the peptides is initiated by mono- or di-valent cations found in culture media or the physiological environment.

The physical size of the nanofibrous, nanoporous, self-assembled-peptide hydrogels relative to cells and proteins, and the peptides' water-structuring abilities, mimic in vivo ECM, allowing cells to proliferate, migrate through, and engage in critical cell-to-cell interactions in the presence of key regulatory molecules. These hydrogels are three-dimensional porous scaffolds that are very difficult or impossible to synthetically produce by known manufacturing techniques. The density of fibers and average pore diameter in the self-assembled-peptide hydrogel correlates with the concentration of self-assembling peptide in the solution that is used to produce the self-assembled-peptide hydrogel. The concentration of self-assembling peptide in the solution can be varied from about 0.5 to about 20 milligrams per milliliter w/v, depending on the contemplated tissue-engineering application of hydrogel required for such application.

The self-assembled-peptide hydrogels comprise self-assembling peptides that are amphiphilic, having alternating repeating units of positively-charged lysine (in KLD) or arginine (in RAD16) and negatively-charged aspartate (in RAD16) and glutamate (in KLD) residues. The self-assembling peptides contain 50 percent charged residues and are characterized by their periodic repeats of alternating ionic hydrophilic and hydrophobic amino acids. Thus, the interaction between the distinct polar and non-polar surfaces facilitates self-assembly of the material into a nanofibrous hydrogel scaffold that can coat surfaces or encapsulate cells.

The amino acids in self-assembling peptides can be selected from d-amino acids, 1-amino acids, or combinations thereof. The hydrophobic amino acids include Ala, Val, Ile, Met, Phe, Tyr, Trp, Ser, Thr and Gly. The hydrophilic amino acids can be basic amino acids, e.g., Lys, Arg, His, Orn; acidic amino acids, e.g., Glu, Asp; or amino acids which form hydrogen bonds, e.g., Asn, Gln. The carboxyl and amino groups of the terminal residues can be protected or not protected. Self-assembled-peptide hydrogels can be formed in a homogeneous mixture of self-complementary and self-compatible peptides or in a heterogeneous mixture of peptides, which are complementary and structurally compatible to each other.

Self-assembled-peptide hydrogels have been found to be stable in aqueous solution, serum and ethanol, and are highly resistant to degradation by heat, alkaline and acidic pH, e.g. pH 1.5 to 11. The hydrogels and nanofibers have also been found to be non-cytotoxic. Being composed primarily of amino acids, the peptide filaments can be digested and metabolized in animals and people. They have a simple composition, are permeable, and are easy and relatively inexpensive to produce in large quantities.

The self-assembly of RAD16 can be observed in tissue culture medium (Dulbecco Modified Eagle's Medium, Gibco BRL, Gaithersburg, Md.) containing calf serum. Self-assembled-peptide hydrogels can also form from self-assembling peptides in phosphate-buffered saline (PBS: 150 millimolar NaCl, 10 millimolar sodium phosphate, pH 7.4). Hydrogels do not form in water but appear after addition of sodium phosphate to a water-peptide solution to an approximate final concentration of 100 milligrams per milliliter. Thus, salt appears to play an important role in the self-assembly process.

Various metal cations have been tested for effectiveness at inducing self-assembled-peptide hydrogel formation from self-assembling peptides. The results indicate that monovalent metal cations induce hydrogel formation, but divalent cations primarily induce unstructured aggregates. Some anions, acetate, $Cl^-$, $SO_4^{-2}$, and $PO_4^{-2}$, and organic ions, $NH_4^+$ and Tris-Cl, were also tested and were not found to induce hydrogel formation.

Concentrations of monovalent metal cations (NaCl) as low as 5 millimolar and as high as 5 Molar have been found to induce self-assembled-peptide hydrogel formation within a few minutes. Thus, hydrogel formation appears to be independent of salt concentration over this wide range. Salt concentrations of less than 5 millimolar may also induce hydrogel formation, but at a slower rate.

The initial concentration of the peptide is a significant factor in the viscosity and integrity of the self-assembled-peptide hydrogel formed. In general, the higher the peptide concentration, the higher the extent of hydrogel formation. Hydrogel can form from initial self-assembling peptide concentrations as low as 0.5 milligram per milliliter. However, hydrogel formed at higher initial peptide concentrations, e.g. about 10 milligram per milliliter, are denser and, thus, likely to be stronger. Therefore, it is preferable when producing the hydrogel to add peptide to a salt solution, rather than to add salt to a peptide solution.

Formation of the hydrogel is on the order of a few minutes and appears to be irreversible. The process is unaffected by pH in the range of 1 to 12 and by temperature, while the peptides tend to precipitate out at pH above 12. The self-assembled-peptide hydrogel can form at temperatures in the range of about 4 to about 90° degrees Centigrade.

Self-assembling peptides may be added to the microporous scaffolds either as a dry powder or a solution. The relative amount of self-assembled-peptide hydrogel to microporous scaffold on a weight to volume basis is effective to provide increased tissue ingrowth and vascularization, as compared to a microporous scaffold of substantially the same composition and construct that does not contain a self-assembled-peptide hydrogel according to the present invention, or a microporous scaffold in combination with hydrogels that are not prepared from self-assembled-peptide utilized in the present invention, such as basement membrane extract. The self-assembly process may be initiated before or after combing with the microporous scaffold, and may be done in vitro or in vivo. The relative amount of self-assembling peptides to microporous scaffold may be about 0.1 to about 10 micrograms peptide per cubic millimeter of scaffold, or about 0.1 to about 5 micrograms peptide per cubic millimeter of scaffold, or about 0.1 to about 1 micrograms peptide per cubic millimeter of scaffold.

Solids may be included in the tissue-engineering scaffolds of the present invention. The solids are of such size as to fit into the pores of the microporous scaffold. Exemplary solids include, but are not limited to, particles of demineralized bone, calcium phosphate particles, bioglass particles or calcium carbonate particles for bone repair, leachable solids for pore creation, and particles of biodegradable polymers not soluble in the solvent system that are effective as reinforcing materials or to create pores as they are absorbed, and nonbiodegradable materials.

Suitable nonbiodegradable materials include biocompatible metals such as stainless steel, cobalt chrome, titanium and titanium alloys, and bioinert ceramic particles, e.g., alumina, zirconia, and calcium sulfate particles. Further, the nonbiodegradable materials may include polymers such as polyethylene, polyvinylacetate, polymethylmethacrylate, silicone, polyethylene oxide, polyethylene glycol, polyurethanes, polyvinyl alcohol, natural biopolymers, e.g., cellulose particles, chitin, keratin, silk, and collagen particles, and fluorinable polymers and copolymers (e.g., polyvinylidene fluoride).

Solids that will render the tissue-engineering scaffold radioopaque, e.g., barium sulfate, may also be added to tissue-engineering scaffolds of the present invention. The solids that may be added also include those that will promote tissue regeneration or regrowth, as well as those that act as buffers. The tissue-engineering scaffolds of the present invention can be used in combination with cells, and/or biological factors and/or bioactives for many tissue engineering applications, such as creation of artificial organs, tissue repair and tissue regeneration. For example pancreatic islets may be incorporated into the hydrogel and a nonwoven scaffold for the treatment of diabetes. Other cells that may be incorporated include stem cells, progenitor cells, postpartum-derived cells as described in co-pending U.S. application Ser. Nos. 10/887,012 and 10/887,446, bone marrow, chondrocytes, osteoblasts, fibroblasts, smooth muscle, myocytes, endothelial, epithelial, hepatocyte and sertoli cells.

Factors, including nutrients, growth factors, inducers of differentiation or de-differentiation, products of secretion, immunomodulators, inhibitors of inflammation, regression factors, biologically active compounds which enhance or allow ingrowth of the lymphatic network or nerve fibers, and drugs, can be incorporated into or provided in conjunction with the present tissue-engineering scaffold. Bioactives that can be added to the scaffold include growth factors, such as transforming growth factor, GDF-5, bone morphogenetic protein, stromal-derived factor and platelet-derived factor; or angiogenic factors, for example VEGF and bFGF.

The tissue-engineering scaffold of the present invention can be used to treat a variety of tissue, including, but not limited to brain, cranial tissue, dura, nerve tissue, spinal disc, lung, cardiac or skeletal muscle, bone, cartilage, tendon, ligament, liver, kidney, spleen, pancreas, bladder, pelvic floor, uterus, blood vessels, breast and skin. The scaffolds can be used to form tissue-engineered organs and portions or specific sections thereof, such as spleen, lung, liver, kidney, pancreas, endocrine glands, cardiac muscle, esophagus, colon, stomach, gall bladder, duodenum, jejunum, penis, vagina, uterus, veins, arteries, urethra, ureta, thyroid, spleen and ileum. The present invention may be also be used for regeneration or repair of muscle facia, such as pelvic floor or rotator cuff, skeletal repair, such as spinal fusion and bone unions, or cartilage repair, such as meniscus or articular cartilage, or soft tissue to bone, such as tendon to bone repair.

It should be clear that various modifications of the present invention can be made without departing from the spirit or scope of the invention. For example, the present invention should not be read to require, or be limited to, a particular material, agent, or cell line described by way of example or illustration set forth below.

Example 1

Dry lay nonwoven microporous scaffolds were prepared from fibers comprising a polylactide-co-glycolide (PLA/PGA) copolymer with a lactide to glycolide ratio of 10:90 and of the type used to make VICRYL® sutures, available from Ethicon, Inc., Somerville, N.J. fibers. The nonwoven scaffolds had a thickness of 2 millimeters and a nominal density of 60 milligrams per cubic centimeter. The nonwoven material was cut into discs of 5-millimeter diameter using a biopsy punch and sterilized using ethylene dioxide. Onto the sterile discs were applied 10 microliters of a) 0.5 percent (w/v) RAD16 self-assembling peptide (3-DMatrix Inc., Cambridge, Mass.) in 50 percent (v/v) water, 10 millimolar Hepes buffer in phosphate buffered saline (PBS), b) 0.5 percent (w/v) KLD self-assembling peptide (3-DMatrix Inc., Cambridge, Mass.) in 50 percent (v/v) water, and c) 8 milligrams per milliliter basement membrane extract, factor-reduced, phenol red-free, sold under the tradename CULTREX (R&D systems, Minneapolis, Minn.) or d) PBS.

The nonwoven discs were then implanted subcutaneous in 200 to 350 gram Long-Evans female rats (Harlan Sprague Dawley Inc., Indianapolis, Ind.) for 14 days. Rats were anesthetized using intraperitoneal injection of 60 milligram per milliliter ketamine hydrochloride (Aveco, Fort Dodge, Iowa) and 10 milligram per milliliter xylazine (Mobay Corp., Shawnee, Kans.). Four incisions were made on the dorsum of each rat, perpendicular to the spine. Two incisions were located transversely over the dorsal lateral thoracic region, one each side of the spine approximately 2 centimeter caudal. The other two incisions were placed transversely over the gluteal muscle area on each side of the spine. A small pocket was created to locate the disc approximately 1 centimeter caudal from the incision and the pocket was tacked with a non-absorbable suture before closing the incision with metal wound clips. Tissue was excised after 14 days and fixed in formalin before processing and sectioning. Sections were stained with hematoxylin & eosin and evaluated for tissue ingrowth and vascularization. To further evaluate vascularization, sections were stained using an antibody to Von Wilebrand's factor (MCA 12; Serotec, Oxford, UK).

Photomicrographs taken of the above-described stained tissue sections showed that a nonwoven scaffold alone, i.e. containing no self-assembled-peptide hydrogel, exhibited tissue ingrowth that was superior to the basement membrane protein. The photomicrographs also showed that tissue ingrowth and vascularization in nonwoven scaffolds combined with RAD16 or KLD self-assembled-peptide hydrogels of the present invention was superior to that observed in nonwoven scaffolds alone or treated with basement membrane extract.

Example 2

Evaluation of 3-D matrix as a scaffold for articular cartilage repair A full-thickness cartilage defect study was conducted to evaluate the potential of using a self-assembled-peptide hydrogel as a scaffold for cartilage tissue engineering. In this study, skeletally mature male New Zealand White rabbits of 4.5 kg or larger size with full closure of the diaphyseal plates were used. Surgical procedures were conducted under general anesthesia that was initiated by an injection of 25 mg/kg body weight of Ketamine and 5 milligram/kilogram of Xyalzine (MWI Veterinarian Supply Company, Nampa, Id.) intramuscularly into the hind extremity. Once anesthetized, a closed endotrachial tube was placed and general anesthesia was maintained with 0.5 to 2.5 percent Isofluorane (MWI Veterinarian Supply Company, Nampa, Id.) delivered in oxygen in a non-rebreathing system. After being placed under general anesthesia, the rabbits were shaved in the knee region of both knees. The knee joint was approached by a medial parapatellar incision. A 4-millimeter diameter full-thickness defect was made in the mid-trochlear region of the distal femur 1 centimeter distal to the fused growth plate using a custom drill bit and guide (DePuy, Inc. Warsaw, Ind.).

Dry lay nonwoven scaffolds as described in Example 1 were utilized. The scaffolds were cut to 4.4-millimeter diameter and sterilized using ethylene dioxide. Onto the sterile discs were applied 10 microliters of a) PBS (nonwoven control), b) 0.5 percent (w/v) KLD self-assembling peptide (3-DMatrix Inc., Cambridge, Mass.) in 50 percent (v/v) water (VICRYL+KLD), or c) 0.5 percent (w/v) RAD16 self-assembling peptide (3-DMatrix Inc., Cambridge, Mass.) in 50 percent (v/v) water, 10 millimolar Hepes buffer in phosphate buffered saline (PBS) (nonwoven+RAD16).

The implants were press fit into the defect and aligned with the surrounding joint surface. The wound was closed using 5-0 VICRYL interrupted sutures. Four rabbits per treatment group were tested. Animals were sacrificed at 8 weeks. The gross observations at necropsy showed that defects treated with nonwoven+KLD or nonwoven+RAD16 appeared more hyaline cartilage-like than defects treated with the nonwoven control. The nonwoven control group appeared to be more fibrous and irregular. Histopathology scoring was performed using both the traditional O'Driscoll scoring system and a modified O'Driscoll scoring system. Results from both of these systems demonstrated that nonwoven+KLD was far better than the nonwoven control or nonwoven+RAD16. Statistically significant improvement (Kruskal-Wallis ANOVA) was seen in the nonwoven+KLD versus the nonwoven control group for the following parameters: Safranin O staining, surface regularity, structural integrity and total score. Statistically significant improvement (Kruskal-Wallis ANOVA) was seen in the nonwoven+RAD16 versus the nonwoven control group for structural integrity.

We claim:

1. A cell-free tissue-engineering scaffold, comprising:
   a) a microporous scaffold comprising a poly(lactide-co-glycolide) co-polymer; and
   b) a nanofibrous, nanoporous hydrogel coating on a surface of said scaffold, wherein said coating is formed from self-assembling peptides selected from the group consisting of NH$_2$-RADARADARADARADA-COOH (SEQ ID NO:1) and NH$_2$-KLDLKLDLKLDL-COOH (SEQ ID NO:2), and wherein at least a portion of said hydrogel is disposed within pores of said microporous scaffold.

2. The cell-free tissue-engineering scaffold of claim 1 wherein said microporous scaffold has a porosity from 85 to 99 percent.

3. The cell-free tissue-engineering scaffold of claim 1 wherein said microporous scaffold comprises pores having an average pore diameter of from 1 to about 2,000 microns.

4. The cell-free tissue-engineering scaffold of claim 1 wherein the thickness of said microporous scaffold is from about 300 to about 3,000 microns.

5. The cell-free tissue-engineering scaffold of claim 1 wherein said hydrogel comprises fibers having a diameter of from about 5 to about 50 nanometers.

6. The cell-free tissue-engineering scaffold of claim 1 wherein said hydrogel comprises pores having an average diameter of from about 50 to about 400 nanometers.

7. The cell-free tissue-engineering scaffold of claim 1 wherein said self-assembling peptides are in a solution which comprises of about 0.5 to about 20 milligrams per milliliter of said self-assembling peptide.

8. The cell-free tissue-engineering scaffold of claim 1 wherein the self-assembling peptides and microporous scaffold have a weight to volume relation of about 0.1 to about 10 micrograms of peptide per cubic millimeter of microporous scaffold.

9. The cell-free tissue-engineering scaffold of claim 1 wherein the self-assembling peptides and microporous scaffold have a weight to volume relation of about 0.1 to about 5 micrograms of peptide per cubic millimeter of microporous scaffold.

10. The cell-free tissue-engineering scaffold of claim 1 wherein the self-assembling peptides and microporous scaffold have a weight to volume relation of about 0.1 to about 1 micrograms of peptide per cubic millimeter of microporous scaffold.

11. The cell-free tissue-engineering scaffold of claim 1, and wherein the self-assembling peptide is NH$_2$-RADARADARADARADA-COOH (SEQ ID NO:1).

12. The cell-free tissue-engineering scaffold of claim 1, wherein the self-assembling peptide is NH$_2$-KLDLKLDLKLDL-COOH (SEQ ID NO:2).

13. A cell-free tissue-engineering scaffold, comprising:
   a) a unitary microporous scaffold formed of a nonbiodegradable polymer suitable for use in tissue-engineering scaffolds; and
   b) a nanofibrous, nanoporous hydrogel coating on a surface of said scaffold wherein said coating is formed from self-assembling peptides selected from the group consisting of NH$_2$-RADARADARADARADA-COOH (SEQ ID NO:1) and NH$_2$-KLDLKLDLKLDL-COOH (SEQ ID NO:2), and wherein at least a portion of said hydrogel is disposed within pores of said microporous scaffold.

14. The tissue-engineering scaffold of claim 13, wherein said nonbiodegradable polymer is selected from the group consisting of aliphatic polyesters, polyacrylates, polymethacrylates, acyl-substituted cellulose acetates, nonbiodegradable polyurethanes, polystyrenes, polyvinyl chloride, polyvinyl flouride, polyvinyl imidazole, chlorosulphonated polyolifins, polyethylene oxide, polyvinyl alcohol, polytetrafluoroethylene, nylon, silicon, poly(styrene-block-butadiene), polynorbomene, ceramics, and metallic alloys.

* * * * *